United States Patent
Tsai

(10) Patent No.: US 7,483,722 B2
(45) Date of Patent: Jan. 27, 2009

(54) MOBILE PHONE WITH A DIATHERMIC FUNCTION

(75) Inventor: Chien-Hung Tsai, Taipei Hsien (TW)

(73) Assignee: Qisda Corporation, Taoyuan County (TW)

( * ) Notice: Subject to any disclaimer, the term of this patent is extended or adjusted under 35 U.S.C. 154(b) by 376 days.

(21) Appl. No.: 11/160,916

(22) Filed: Jul. 14, 2005

(65) Prior Publication Data

US 2006/0014572 A1   Jan. 19, 2006

(30) Foreign Application Priority Data

Jul. 16, 2004   (TW) ............... 93121356 A

(51) Int. Cl.
*H04B 1/38*   (2006.01)
*H04M 1/00*   (2006.01)

(52) U.S. Cl. .............. 455/572; 455/573; 455/574; 455/575.1; 379/413; 379/422; 379/433.03

(58) Field of Classification Search ............ 455/571, 455/572, 573, 574, 556.1, 575.1, 575.6; 379/413, 379/422, 433.03, 428.04
See application file for complete search history.

(56) References Cited

U.S. PATENT DOCUMENTS

| 6,038,457 | A * | 3/2000 | Barkat ................. 455/556.1 |
| 6,528,970 | B1 * | 3/2003 | Liu et al. ................ 320/107 |
| 6,555,990 | B1 * | 4/2003 | Yang ..................... 320/113 |
| 2002/0075161 | A1 * | 6/2002 | Raffel et al. .......... 340/825.69 |
| 2003/0231026 | A1 * | 12/2003 | Bazarjani ................ 324/711 |
| 2004/0230226 | A1 * | 11/2004 | Bingham et al. ............ 607/3 |
| 2004/0259607 | A1 * | 12/2004 | Sea Weng et al. ....... 455/575.2 |
| 2005/0021115 | A1 * | 1/2005 | Yue ..................... 607/114 |
| 2005/0221859 | A1 * | 10/2005 | Wang et al. ............. 455/557 |

FOREIGN PATENT DOCUMENTS

JP   07-313570   * 5/1995

* cited by examiner

*Primary Examiner*—Tuan A Pham

(57) ABSTRACT

A mobile communication device includes a housing, a processing module installed inside the housing for controlling the mobile communication device, a power supply module for supplying the electric power of the mobile communication device, a first connecting port installed on the housing and connected to the power supply module for outputting voltage transmitted from the power supply module, and a diathermic module connected to the first connect port including an electrode pad for providing an electrical treatment according to the voltage transmitted from the first connect port.

7 Claims, 8 Drawing Sheets

| Control signal | Input voltage(Vin) | First output voltage | Second output voltage |
|---|---|---|---|
| 0 | -33V | -6V | -33V |
| 1 | -6V | -6V | 0V |

Fig. 3

MOBILE PHONE WITH A DIATHERMIC FUNCTION

BACKGROUND OF THE INVENTION

1. Field of the Invention

The invention relates to a mobile communication device, and more particularly, to a mobile communication device with a diathermic function.

2. Description of the Prior Art

Mobile Phones have become highly popular electronic devices in recent years. The reduction in cost of the mobile phones has placed them in the affordable range of most people. Due to the rapid progress in technology, more functional and powerful mobile phones are constantly being invented. In order to meet costumers' demands, the mobile phone manufacturers often add many new functions and techniques to the mobile phone. For example, in the most modern mobile phones, a digital camera function and external keyboards are embedded in the mobile phone, both increasing convenience and enhancing the users' lifestyle.

Today's mobile phones utilize LEDs or OLEDs. Therefore, they need a DC-DC converter with a charge-pump function to raise the voltage of the mobile phone battery so that the above-mentioned devices can be driven. If the high voltage outputted by the DC-DC converter can be utilized to provide power to other devices (e.g. the new functions mentioned above), the value of the whole mobile phone will be increased.

SUMMARY OF THE INVENTION

It is therefore one of the primary objectives of the claimed invention to provide a mobile communication device with a diathermic function, to solve the above-mentioned problem.

According to an exemplary embodiment of the claimed invention, a mobile communication device is disclosed. The mobile communication device comprises: a housing; a processing module installed inside the housing for controlling the mobile communication device; a power supplying module for supplying needed power of the mobile communication device; a first connecting port installed on the housing and electrically connected to the power supplying module for a voltage outputted by the power supplying module; and a diathermic module electrically connected to the first connecting port; wherein the diathermic module comprises an electrode pad for providing an electrical treatment according to the voltage outputted by the first connecting port.

These and other objectives of the present invention will no doubt become obvious to those of ordinary skill in the art after reading the following detailed description of the preferred embodiment that is illustrated in the various figures and drawings.

BRIEF DESCRIPTION OF THE DRAWINGS

FIG. 3 is a logic relationship diagram of an input signal and an output signal of a logic unit.

DETAILED DESCRIPTION

Figure 1:
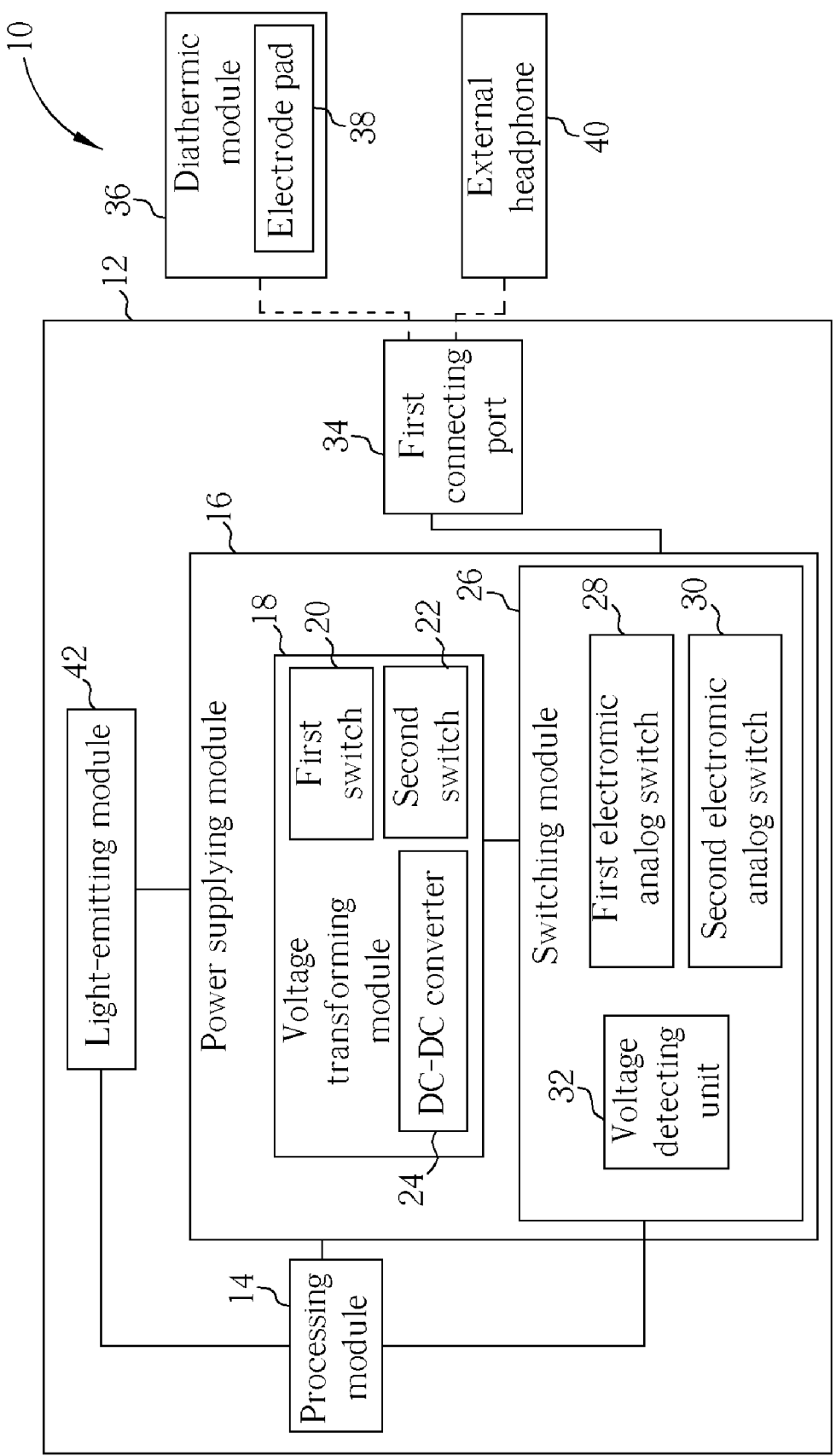
FIG. 1 is a block diagram of a mobile communication device according to the present invention.

Please refer to FIG. 1, which is a block diagram of a mobile communication device 10 according to the present invention. The mobile communication device 10 can be a mobile phone. The mobile communication device 10 comprises a housing 12 for covering inner devices of the mobile communication device 10, a processing module 14 installed inside the housing 12 for controlling the mobile communication device 10, and a power supplying module 16 for supplying needed power to the mobile communication device 10. The power supplying module 16 comprises a voltage transforming module 18 for transforming a voltage generated by the power supplying module 16 or received from external circuits into another voltage having a different voltage level. The voltage transforming module comprises a first switch 20, a second switch 22, and a DC-DC converter 24. The power supplying module 16 further comprises a switching module 26 electrically connected to the processing module 14 for switching operation modes of the mobile communication device 10. The switching module 26 comprises a first analog switch 28, a second analog switch 30, and a voltage detecting unit 32 electrically connected to the processing module 14 for detecting the voltage level of the switching module 26 and transmitting the voltage level to the processing module 14. The mobile communication device 10 further comprises a first connecting port 34 connected to the power supplying module 16 for outputting the voltage transmitted from the power supplying module 16. The first connecting port 34 can be connected to a diathermic module 36, wherein the diathermic module 36 comprises an electrode pad 38 for providing a diathermic function according to the voltage transmitted from the first connecting port 34. Furthermore, the first connecting port 34 can be connected to an external headphone 40 for providing a phone communication to users. In addition, the mobile communication device 10 further comprises a light-emitting module 42 electrically connected to the power supplying module 16 for receiving the voltage outputted by the power supplying module 16 to emit lights, wherein the light-emitting module can comprise devices such as LEDs or OLEDs.

Figure 2:
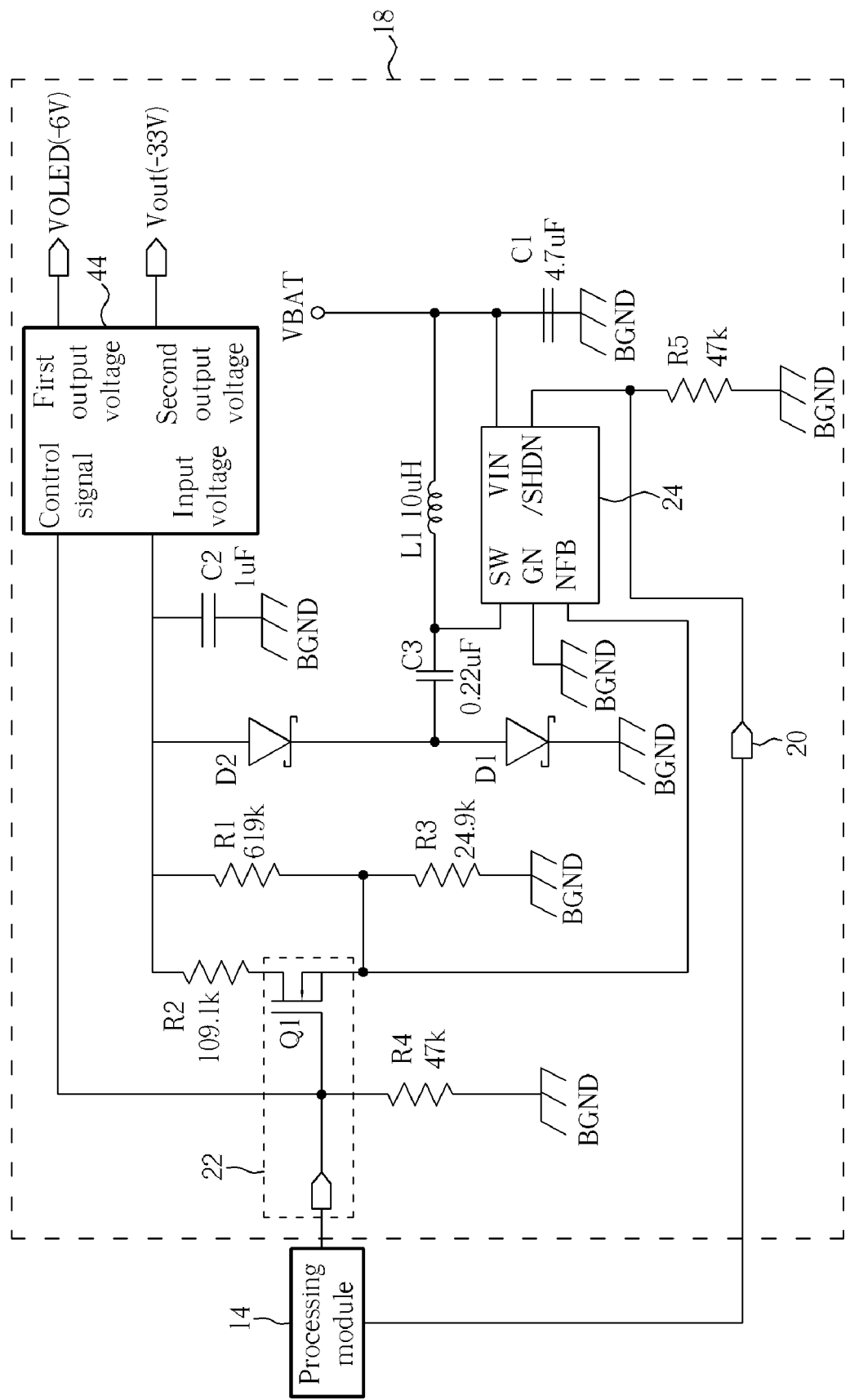
FIG. 2 is a circuit diagram of a voltage transforming module.

Please refer to FIG. 2, which is a circuit diagram of the voltage transforming module 18 shown in FIG. 1. In this embodiment, a DC-DC converter IC (for example, LT1617 from Linear Technology) is utilized to achieve the DC-DC converter 24 of the voltage transforming module 18. The voltage transforming module 18 utilizes the second switch 22 to control the voltage output. When a transistor Q1 of the second switch 22 is controlled to be a high level voltage by the processing module 14, the transistor Q1 is turned on and the DC-DC converter 24 is controlled by a divided voltage divided by the three resistors R1, R2, and R3. Therefore, an input voltage Vin is inputted into a logic unit 44. Here, the input voltage Vin can be calculated from a datasheet of the LT 1617 IC. When the pin NFB is fixed to receive a voltage 1.23V, the voltage −Vin can be determined by the divided voltage because of the resistors on the current route.

$$-Vin = 1.23*[1+(R1\|R2)/R3]+(R1\|R2)*2*10^{-6}$$
$$= 1.23*[1+(619K\|109.1K)/24.9K]+(619K\|109.1K)*2*10^{-6}$$
$$= 1.23*(1+92.75K/24.9K)+92.75K*2*10^{-6}$$
$$= 6.14+0.18$$
$$= 6.32\ (V)$$
$$Vin = -6.32\ (V)$$

In the above equation, R1‖R2=(R1*R2)/(R1+R2), and 1.23V is a reference voltage in the pin NFB of the IC LT 1617.

Therefore, the voltage −6V can be obtained, and the voltage −6V can be utilized to supply the light-emitting module 42. But at this time, the voltage can not provide enough voltage to the diathermic module 36. When the transistor Q1 is a low-level voltage controlled by the processing module 14, the transistor Q1 is turned off, and the DC-DC converter 24 is controlled only by a divided voltage divided by the resistors R1 and R3. Then the input voltage Vin can be inputted to the logic unit 44 through the following equation:

$$-Vin = 1.23*[1+(R1/R3)]+R1*2*10^{-6}$$
$$= 1.23*[1+(619K/24.9K)]+619K*2*10^{-6}$$
$$= 31.8+1.2$$
$$= 33\ (V)$$
$$Vin = -33\ (V)$$

Therefore, the input voltage Vin is −33V. The input voltage −33V can be inputted to the diathermic module 36 to drive the diathermic function. Please refer to FIG. 3, which is a logic relationship diagram of an input signal and an output signal of a logic unit 44. When the second switch 22 receives a low-level (0) control signal and transfers the signal to the logic unit 44, the input voltage Vin outputted by the DC-DC converter 24 is −33V, and the logic unit 44 can output a first output voltage −6V and a second output voltage −33V, where the first output voltage −6V can be utilized to supply the light-emitting module 42, and the second output voltage −33V can be utilized to supply the diathermic module 36. When the second switch 22 receives a high-level (1) control signal and transfers the signal to the logic unit 44, the DC-DC converter 24 can output a −6V input voltage Vin, and the logic unit 44 can output a first output voltage −6V. The first output voltage −6V can be utilized to supply the light-emitting module 42. At this time, the second output voltage is 0V. In other words, a voltage is not outputted to the diathermic module 36, so the diathermic module 36 does not operate.

Figure 4:
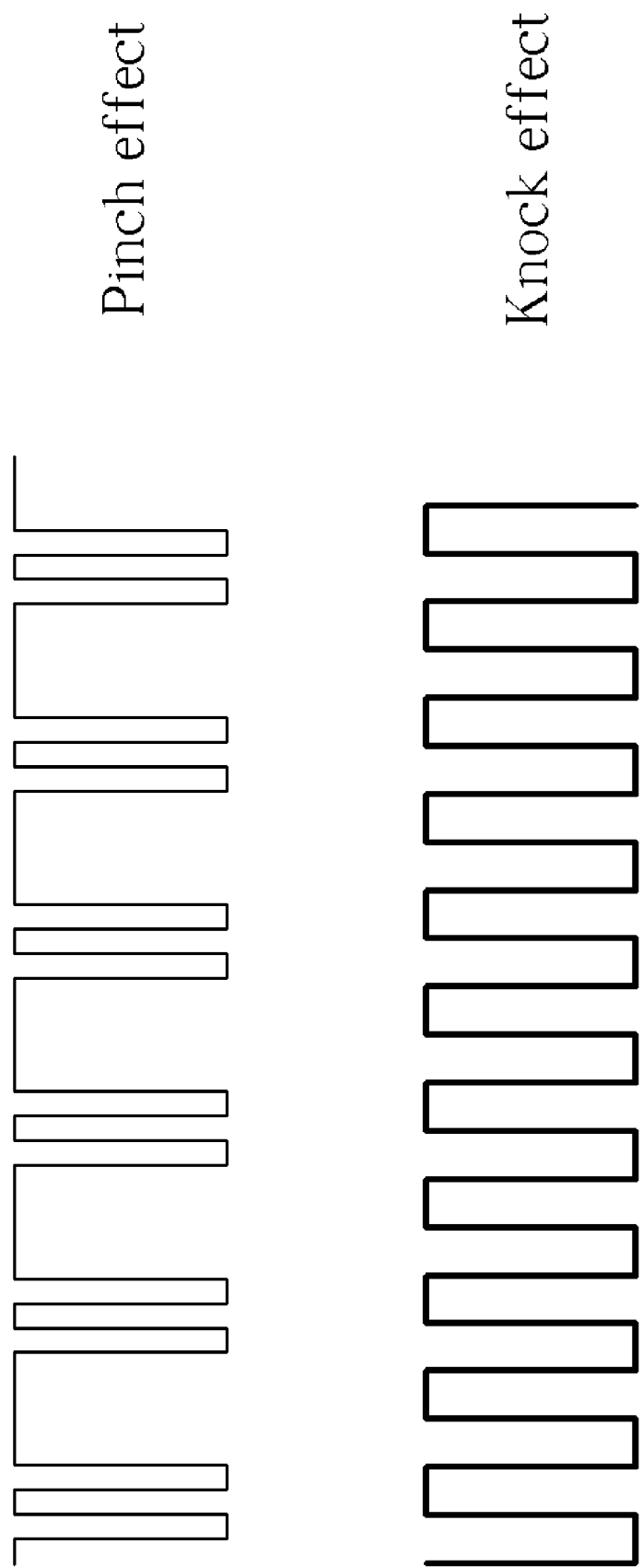
FIG. 4 is a diagram illustrating diathermic modes of a diathermic module corresponding to a voltage of different pulses outputted by the voltage transforming module.

Furthermore, the first switch 20 of the voltage transforming module 18 can be utilized to determine the pulse timing of the outputted voltage of the voltage transforming module 18. The first switch 20 is connected to the SHDN pin of the DC-DC converter 24 and utilized to receive a signal transferred from the processing module 14 to control the pulse timing of the output voltage. When the voltage outputted by the DC-DC converter 24 is −33V, the voltage transforming module 18 can output a −33V voltage to supply the diathermic module. The first switch 20 can control the pulse timing of the voltage inputted to the diathermic module 36. Please refer to FIG. 4, which is a diagram illustrating diathermic modes of a diathermic module 36 corresponding to a voltage of different pulses outputted by the voltage transforming module 18. When the voltage transforming module 18 outputs a pulse wave as the top wave (that is, a wave having interlaced wider square waves and narrow square waves) in FIG. 4, the diathermic module 36 can have a diathermic mode of a pinch effect. On the other hand, when the voltage transforming module 18 outputs a pulse wave as the bottom wave (a uniform square wave) in FIG. 4, the diathermic module 36 can have a diathermic mode of a knock effect. In other words, different pulse timings can achieve different diathermic effects.

Figure 5:
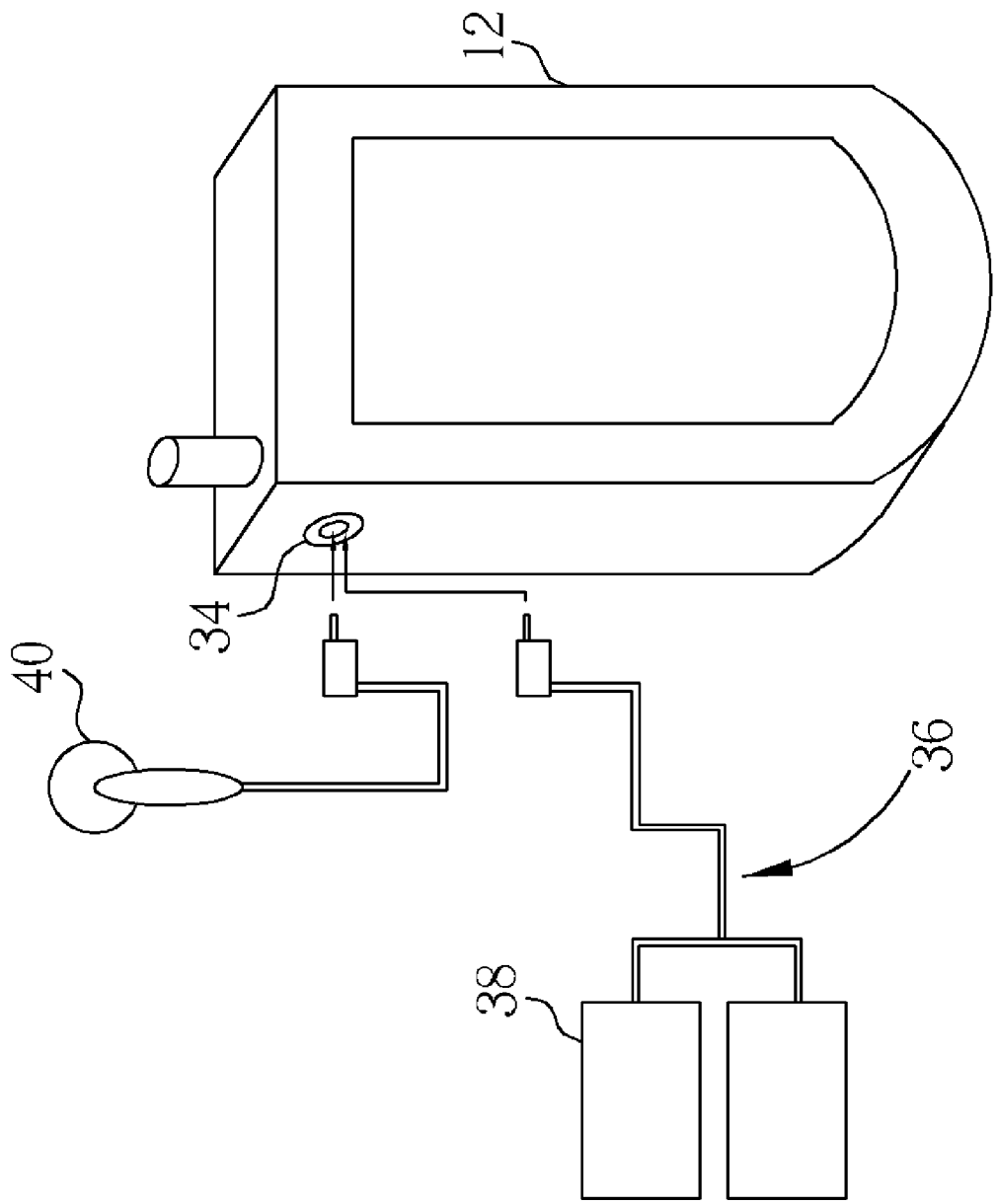
FIG. 5 is a diagram of a first embodiment of an external headphone and electrode pads of a diathermic module sharing a first connecting port according to the present invention.
Figure 6:
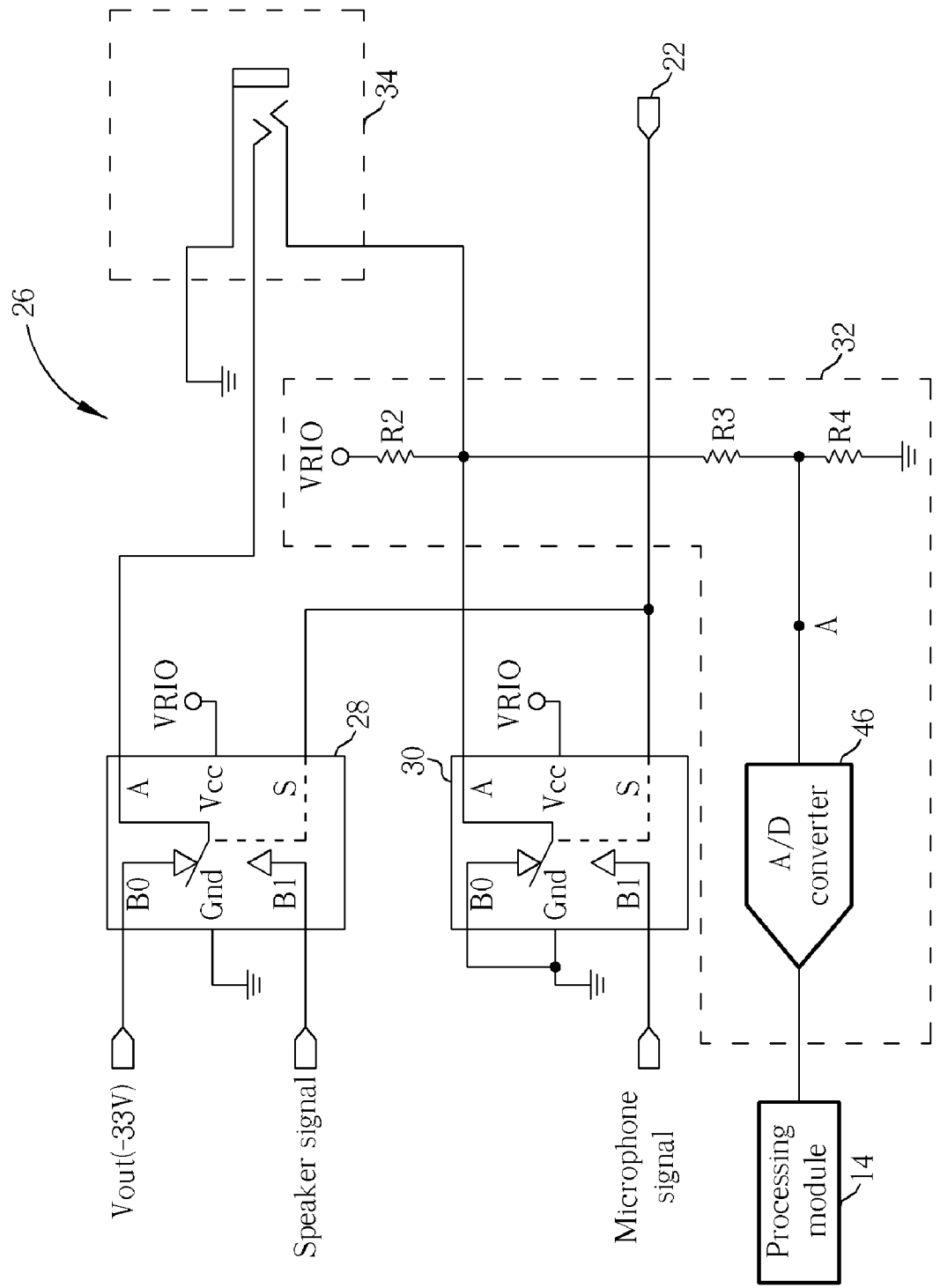
FIG. 6 is a diagram of a first embodiment of an external devices switching module according to the present invention.

Please refer to FIG. 5, which is a diagram of a first embodiment of the external headphone 40 and the electrode pad 38 of the diathermic module 36 sharing the same first connecting port 34. The external headphone 40 and the electrode pad 38 can be plugged into the first connecting port 34 in an external device way. In other words, the external headphone 40 and the electrode pad 38 can share the same socket. Please refer to FIG. 6, which is a circuit diagram of a first embodiment of the external devices switching module 26. The first electronic analog switch 28 of the external devices switching module 26 is utilized to receive a second output voltage transferred from the voltage transforming module 18 (that is, the −33V voltage), a speaker signal of the external headphone 40, and a signal transferred from the second switch 22, to determine whether to output the second output voltage or the speaker signal. In addition, the second electronic analog switch 30 of the external devices switching module 26 is utilized to receive a microphone signal of the external headphone 40, and a signal transferred from the second switch 22 and to determine if the microphone signal is outputted. The diathermic module 36 and the external headphone 40 can share the first connecting port 34. Furthermore, the first electronic analog switch 28 and the second electronic analog switch 30 can be utilized to switch to the diathermic mode or external headphone mode. The pin of the first electronic analog switch 28 and the second electronic analog switch 30 is utilized to receive the signal transferred from the second switch 22. When the second switch 22 transfers a low-level signal (0), the first electronic analog switch 28 and the second electronic analog switch 30 are both switched to B0 route. At this time, the first electronic analog switch 28 outputs a −33 V voltage to the first connecting port 34. The second electronic analog switch 30 is connected to the ground. At this time, the −33V voltage is outputted through the first connecting port to the electrode pad 38 of the diathermic module 36 to provide the diathermic effect. Furthermore, when the second switch 22 transfers a high-level (1) voltage, the first electronic analog switch 28 and the second electronic analog switch 30 are both switched into the B1 route. At this time, the first electronic analog switch 28 is connected to the speaker signal of the external headphone, and the second electronic analog switch is connected to the microphone signal of the external headphone 40. Therefore, the external headphone can be utilized at this time.

Please refer to FIG. 6 again. But there are still two potential problems here. Firstly, users may incorrectly switch the mobile communication device 10 into the diathermic mode when the external headphone 40 is plugged into the first connecting port. This may cause the external headphone 40 to be broken due to the high-level voltage. Secondly, users may switch the mobile communication device 10 into the external headphone mode after the diathermic module 36 is plugged into the first connecting port. This may cause the diathermic module to fail to operate. In order to prevent the above-mentioned problems, the voltage detecting unit 32 of the external switching 26 can be utilized for detecting the voltage of the external devices switching module 26. This is because the resistor characteristics of the external headphone 40 and the diathermic module 36 are different. In other words, when the resistor R2 is biased by the VRIO, and the resistors R3 and R4 divide the voltage, the external headphone 40 and the diathermic module 36 have different voltages at point A. The voltage detecting unit 32 comprises an analog/digital converter 46. Therefore, the voltage at point A is inputted into the A/D converter 46 and the A/D converter 46 can transform the voltage into a digital signal and transfer the digital signal to the processing module 14. Therefore, the function of detecting which device is plugged into the first connecting port 34 is achieved so that this can prevent the above-mentioned incorrect operations.

As mentioned above, users can select a needed mode (diathermic mode or external headphone mode) and input the needed diathermic mode through a user interface of the mobile communication device 10. In other words, users can select the diathermic mode and select the needed diathermic mode through the processing module 14 outputting corresponding signals to the first switch 20 and the second switch 22. Furthermore, the mobile communication device 10 can be automatically switched into a certain operation mode according to a detecting result of the voltage detecting unit 32 of the external devices switching module 26 because the voltage detecting unit can detect which device is connected to the first connecting port 34.

Figure 7:
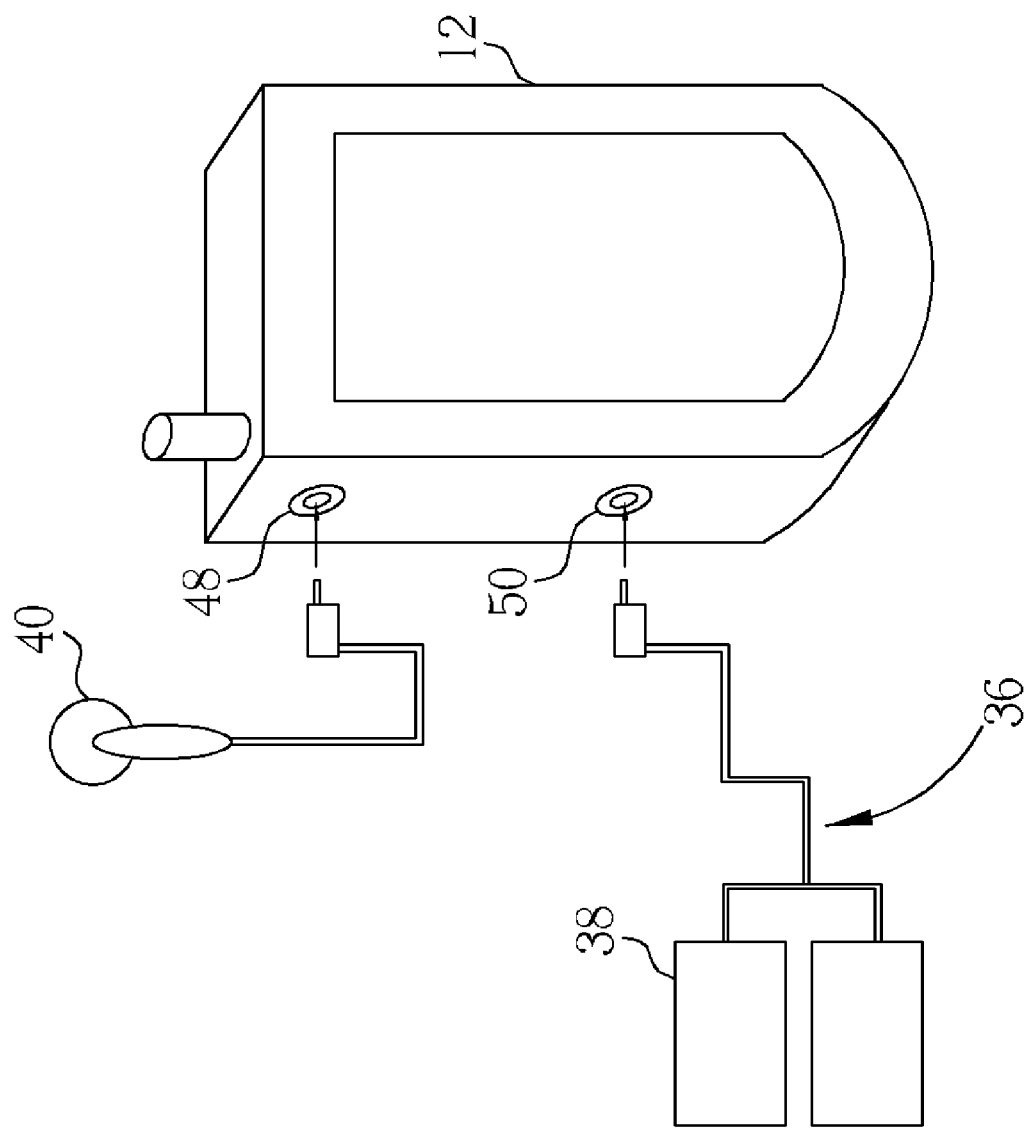
FIG. 7 is a diagram of a second embodiment of the external headphone and the electrode pads of the diathermic module utilizing different connecting ports according to the present invention.
Figure 8:
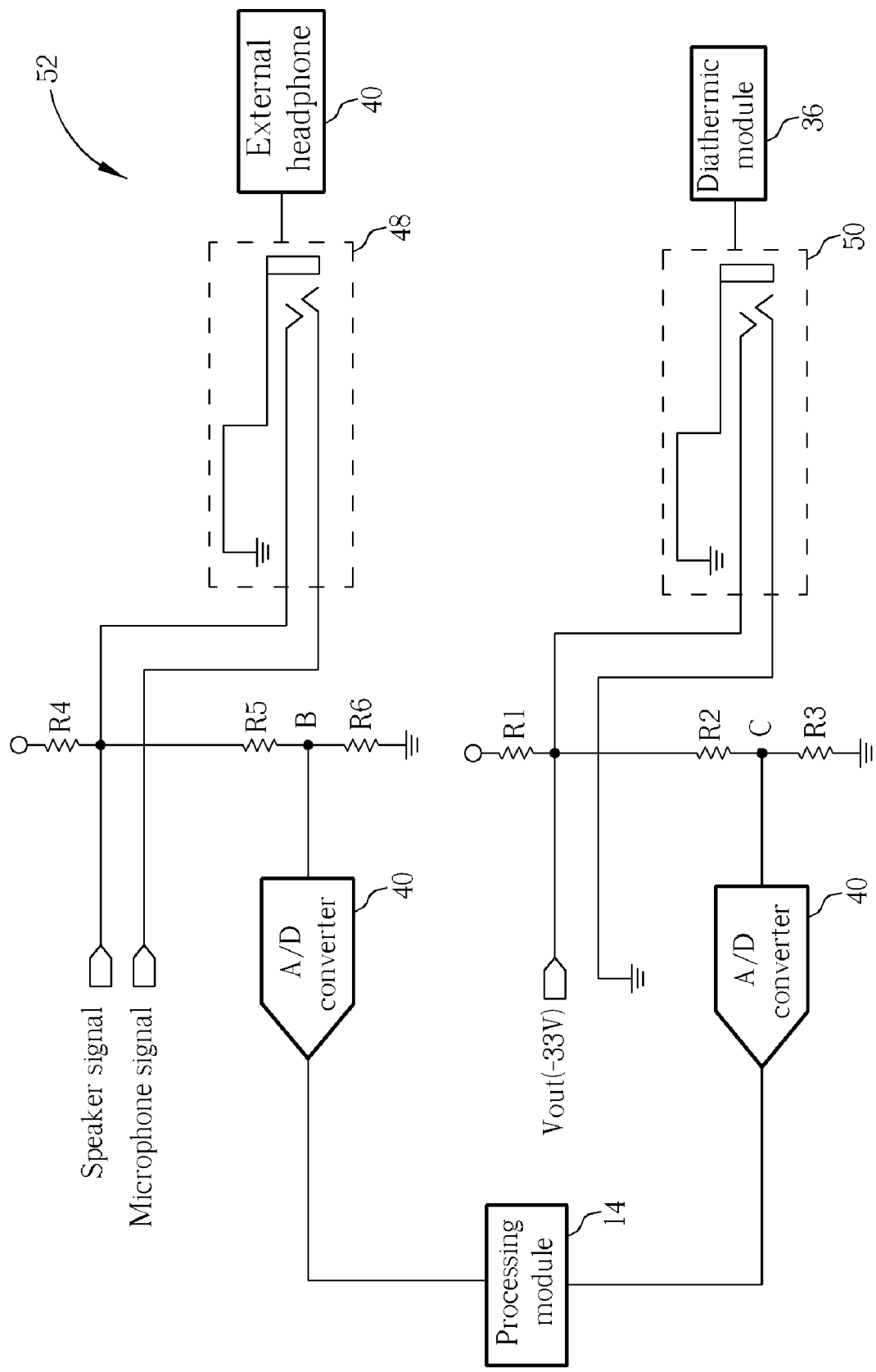
FIG. 8 is a second embodiment of the external devices switching module according to the present invention.

If the housing 12 of the mobile communication device 10 has enough space, the mobile communication device 10 can be designed to connect the diathermic module 36 and the external headphone 40 to different connecting ports. Please refer to FIG. 7, which is a diagram of a second embodiment of the external headphone 40 and the electrode pads 38 of the diathermic module 36 connected to different connecting ports according to the present invention. The external headphone 40 can be designed to be connected to the connecting port 48 on the housing 12. The electrode pad 38 of the diathermic module 36 can be connected to a third connecting port 50 on the housing 12. In other words, the external headphone 40 and the diathermic module 36 utilize different connecting ports. Please refer to FIG. 8, which is a second embodiment of the external devices switching module 52 according to the present invention. In this embodiment, the electronic analog switches shown in FIG. 6 can be ignored. The external devices switching module 52 utilizes an individual route to provide voltage or signals to the diathermic module 36 and the external headphone 40. Furthermore, the two A/D converters 46 can respectively detect voltages at point B and point C, transform the voltages into digital signals, and transfer the digital signals to the processing module 14. Therefore, they can detect whether the second connecting port 48 is connected to the external headphone 40, and they can detect whether the third connecting port 50 is connected to the diathermic module 36. Because the external headphone function and the diathermic function are respectively completed through independent circuits, the mobile communication device 10 can utilize the diathermic function even if the external headphone function is simultaneously utilized. Therefore, the convenience of utilization is raised.

In contrast to the prior art, the present invention mobile communication device can well utilize a high-level voltage transformed by the DC-DC converter to provide needed power to an external diathermic module. Furthermore, the present invention can add fewer devices to increase functions of the mobile communication device. In other words, the present invention mobile communication device adds a diathermic module to benefit users.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A mobile communication device comprising:
  a housing;
  a processing module installed inside the housing for controlling the mobile communication device;
  a power supplying module for supplying needed power of the mobile communication device, the power supplying module comprising:
    an external devices switching module electrically connected to the processing module; and
    a voltage transforming module for outputting a first voltage and a second voltage, the voltage transforming module comprising a first switch for determining whether the first voltage or the second voltage is outputted;
  a first connecting port installed on the housing and electrically connected to the power supplying module for transmitting the first voltage outputted by the voltage transforming module;
  a light-emitting module electrically connected to the voltage transforming module for receiving the second voltage outputted by the voltage transforming module to emit lights;
  a diathermic module electrically connected to the first connecting port, the diathermic module comprising an electrode pad for providing an electrical treatment according to the voltage outputted by the first connecting port; and
  an external headphone electrically connected to the first connecting port on the housing for providing a phone communication; wherein the external devices switching module switches operation modes of the mobile communication device when the diathermic module or the external headphone is connected to the first connecting port;
  wherein the external devices switching module comprises:
    a first electronic analog switch for receiving the first voltage outputted by the voltage transforming module, a first signal of the external headphone, and a signal transferred from the first switch to determine whether the first voltage or the first signal is outputted according to the signal from the first switch;
    a second electronic analog switch for receiving a second signal of the external headphone and the signal transferred from the first switch to determine if the second signal is transferred according to the signal of the first switch.

2. The mobile communication device of claim 1, wherein the voltage transforming module comprises a second switch for determining a timing of a pulse of the first voltage outputted by the voltage transforming module.

3. The mobile communication device of claim 1, wherein the first signal is a speaker signal of the external headphone, and the second signal is a microphone signal of the external headphone.

4. The mobile communication device of claim 1, wherein the first signal is a microphone signal of the external headphone, and the second signal is a speaker signal of the external headphone.

5. The mobile communication device of claim 1, wherein the operation modes comprise a diathermic mode and an external headphone mode.

6. The mobile communication device of claim 1, wherein the external devices switching module comprises a voltage detection unit electrically connected to the processing module for detecting the voltage of the external devices switching module and transferring the voltage to the processing module.

7. The mobile communication device of claim 1, wherein the power supplying module comprises a DC-DC converter.

* * * * *